United States Patent [19]

Townley et al.

[11] 4,068,324
[45] Jan. 17, 1978

[54] PLATFORM SUPPORTED HIP PROSTHESIS

[75] Inventors: Charles O. Townley, Port Huron, Mich.; Allan Vegell, Warsaw; Daniel G. Eaby, Winona Lake, both of Ind.

[73] Assignee: Bio-Dynamics Inc., Indianapolis, Ind.

[21] Appl. No.: 760,622

[22] Filed: Jan. 19, 1977

[51] Int. Cl.² ............................................... A61F 1/24
[52] U.S. Cl. ..................... 3/1.913; 3/1.912; 128/92 C; 128/92 CA
[58] Field of Search .............. 3/1, 1.91–1.913; 128/92 C, 92 CA

[56] References Cited

U.S. PATENT DOCUMENTS

| | | | |
|---|---|---|---|
| 3,466,670 | 9/1969 | Christiansen | 3/1.913 |
| 3,608,096 | 9/1971 | Link | 128/92 C X |
| 3,894,297 | 7/1975 | Mittelmeier et al. | 3/1.912 |
| 3,965,490 | 6/1976 | Murray et al. | 3/1.913 |
| 4,021,865 | 5/1977 | Charnley | 3/1.913 |
| 4,031,571 | 6/1977 | Heimke et al. | 128/92 CA |

*Primary Examiner*—Ronald L. Frinks
*Attorney, Agent, or Firm*—Woodard, Weikart, Emhardt & Naughton

[57] ABSTRACT

A hip joint prosthesis consisting of an artificial femur head and an artificial acetabular socket. The femur head includes a ball head which is received in the acetabular socket, a neck connecting the ball head to a platform and an arcuate stem which is T-shaped in cross section and extends from the platform for insertion into the medullar cavity in a femur. A recess located on the lateral portion of the platform and several steps located along the medial portion of the stem are further provided to securely anchor the prosthesis when it is cemented into the medullar cavity.

5 Claims, 11 Drawing Figures

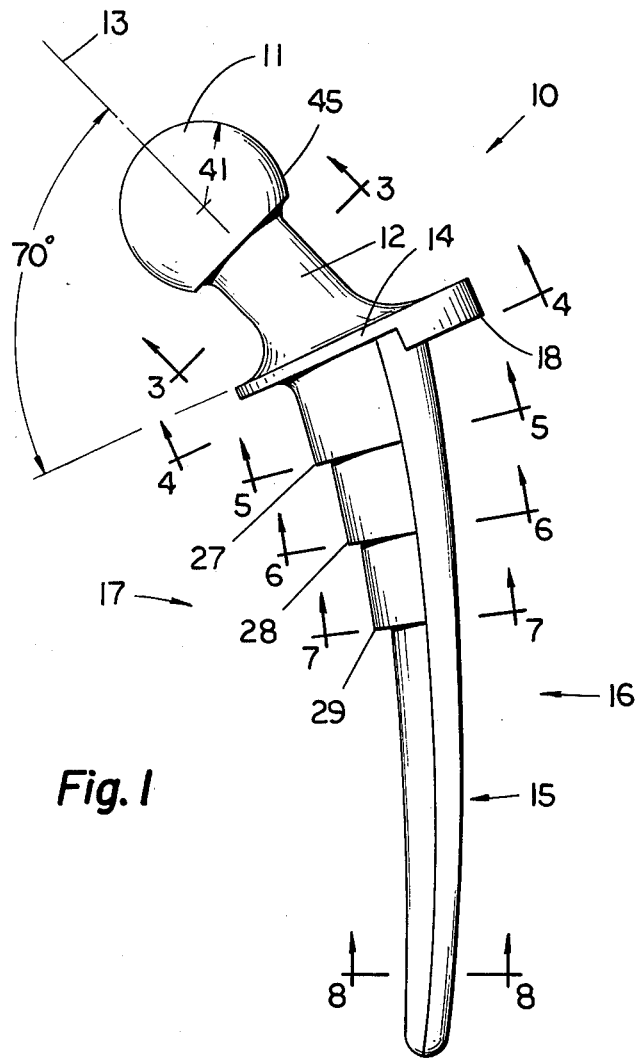
Fig. 1
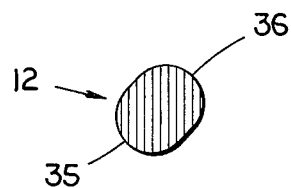
Fig. 3
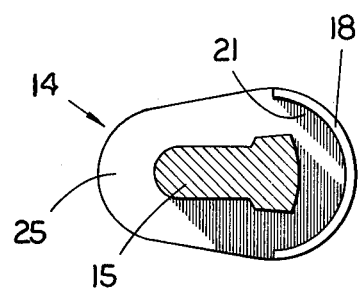
Fig. 4
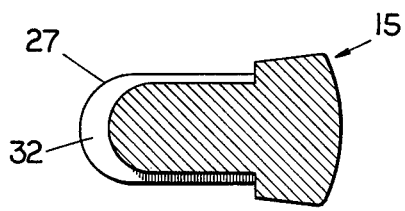
Fig. 5
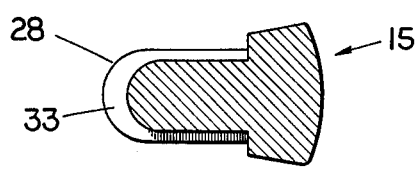
Fig. 6
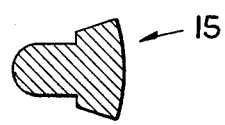
Fig. 8
Fig. 7

PLATFORM SUPPORTED HIP PROSTHESIS

BACKGROUND OF THE INVENTION

1. Field of the Invention

The present invention relates to a new and improved hip joint prosthesis.

2. Description of the Prior Art

Artificial hip joint prostheses have been long known to the art. At first, only replacement of the femur head was practiced. Now, operations for the replacement of the acetabular socket in the pelvis in addition to the femur head are commonly practiced.

Three major problems are commonly encountered in such operations. First is the problem of securely anchoring the prosthesis in the medullar bone cavity. Early attempts using inadequate anchorage often resulted in a resorption phenomena of the supporting bone. Such problems are explained in U.S. Pat. No. 3,894,297 to Mittelmeir et al. Such resorption phenomena caused the prosthesis shaft to loosen in the medullar cavity forcing the prosthesis further into the femur. Bone cement was later employed to circumvent this problem, but bone resorption and prosthesis loosening were still often encountered. Various other securing means have been used, such as screws (U.S. Pat. No. 3,781,917 and No. 3,782,373), screws and knife blades (U.S. Pat. No. 3,843,975), packed bone chips (U.S. Pat. No. 3,740,769), porous sintered powder (U.S. Pat. No. 3,808,606), teeth (U.S. Pat. No. 3,685,058 and No. 3,874,003), and ribs (U.S. Pat. No. 3,894,297). But anchoring the prosthesis in the medullar cavity remains a major problem.

Second, the strong resultant forces applied to the prosthesis during normal loading have often deformed or permanently damaged the artificial joint necessitating its replacement by a further operation. A variety of prosthesis configurations, as disclosed in the above patents, have been employed to overcome these resultant stresses with varying degrees of success.

Third, the problem of prosthesis wear remains a major concern. In many artificial joints, the ball head is mounted on a pin or arm connected to the femoral stem. Any binding or friction that develops at this connection may cause considerable attrition and may even require a further operation.

The present invention remedies all of these problems. First, the platform has a perpendicularly-extending lip on its lower lateral portion which defines a recess. This lip embeds into the cement during insertion of the prosthesis into the medullar cavity and the recess compresses the cement on the lateral side of the prosthesis thereby securely anchoring the prosthesis in the medullar cavity and resisting the later tendency of the prosthesis to rotate and tilt medially. A plurality of steps are also provided on the medial portion of the stem both anteriorly and posteriorly which compress the cement on the medial portion of the prosthesis and increase the contact surface thereby enhancing the anchoring effect. The T-shaped configuration of the stem also assists in anchoring the prosthesis in the medullar cavity.

Second, the orientation of the platform relative to the common axis of the ball head and the neck is such that the platform is more horizontal and thus more directly aligned with the resultant forces and can more evenly distribute these forces throughout the prosthesis and supporting bone and anchoring cement. These stresses are also dispersed in the present invention by the aforementioned steps along the stem and by the oval cross-sectional shape of the neck.

Third, the problem of wear is eliminated in the present invention because the prosthesis is one integral unit. No friction or resultant attrition is therefore encountered.

SUMMARY OF THE INVENTION

One embodiment of the present invention is a platform supported hip prosthesis consisting of a ball head for insertion into an acetabular socket, a neck connecting the ball head to a platform, and an arcuate stem for insertion into the medullar cavity in a femur.

More specifically, the neck and ball head have a common axis and the platform is oriented at an angle relative to this axis to better distribute the forces exerted on the prosthesis during loading. The platform also has a perpendicularly-extending lip on its lower lateral portion which forms a recess for compressing the cement in the medullar cavity thereby more securely anchoring the prosthesis. The stem is T-shaped in cross section and has several steps on its medial portion for further compressing the cement and dispersing the resultant forces on the prosthesis. These forces are also better handled in the present invention by the oval cross section of the neck, with its thicker portion extending medially and laterally thereby strengthening the neck in those directions.

One object of the present invention is to provide a prosthesis that may be more securely anchored in the medullar cavity of a femur without requiring drilling or the use of screws or other external means.

Another object of the present invention is to provide a prosthesis that will better withstand and disperse the applied forces during normal loading.

Another object of the present invention is to provide a prosthesis that escapes the wear and stability problems of previously known prostheses.

BRIEF DESCRIPTION OF THE DRAWINGS

FIG. 1 is an anterior view of the platform supported hip prosthesis of the present invention.

FIG. 3 is a cross-sectional view of the neck taken along line 3—3 in FIG. 1.

FIG. 4 is a cross-sectional view of the stem taken along line 4—4 in FIG. 1.

FIG. 5 is an enlarged cross-sectional view of the stem taken along line 5—5 in FIG. 1.

FIG. 6 is an enlarged cross-sectional view of the stem taken along line 6—6 in FIG. 1.

FIG. 7 is an enlarged cross-sectional view of the stem taken along line 7—7 in FIG. 1.

FIG. 8 is an enlarged cross-sectional view of the stem taken along line 8—8 in FIG. 1.

DESCRIPTION OF THE PREFERRED EMBODIMENT

Figure 2:
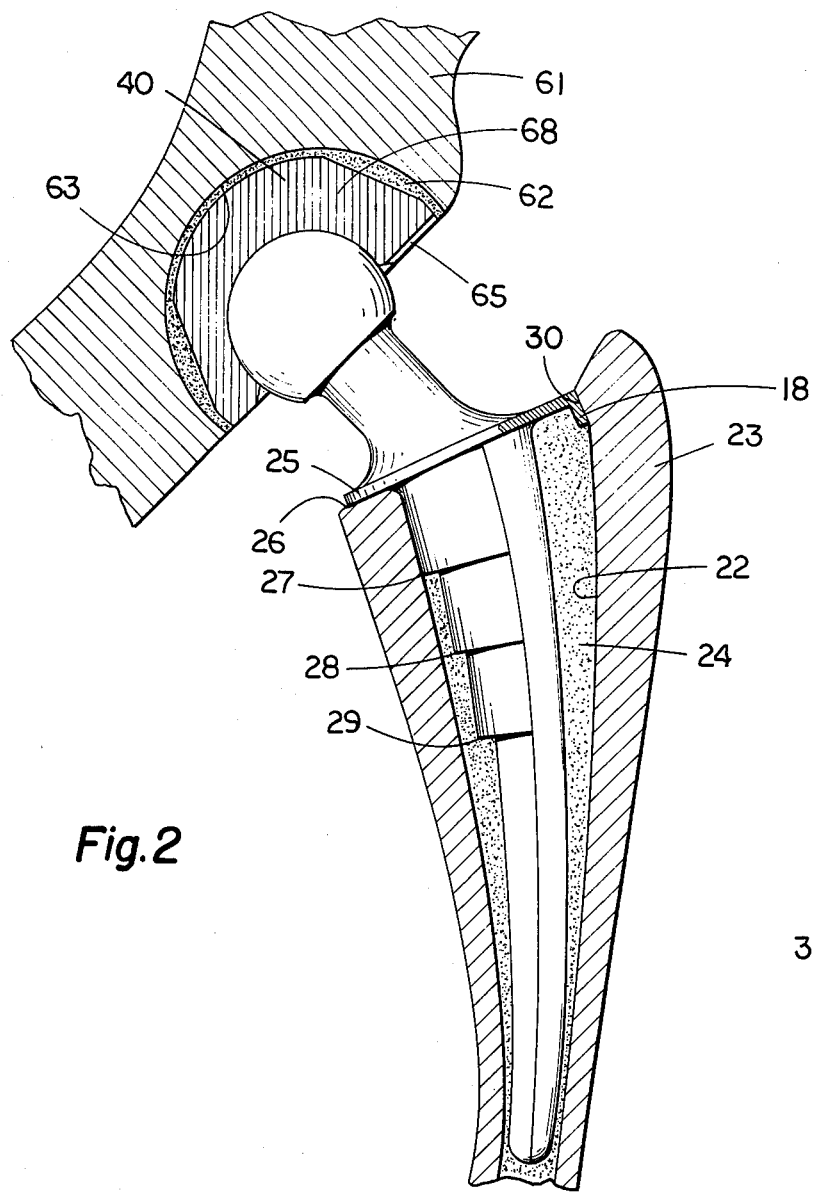
FIG. 2 is a sectional anterior view of the hip prosthesis in FIG. 1 after insertion into a medullar cavity and an artificial acetabular cup.
Figure 9:
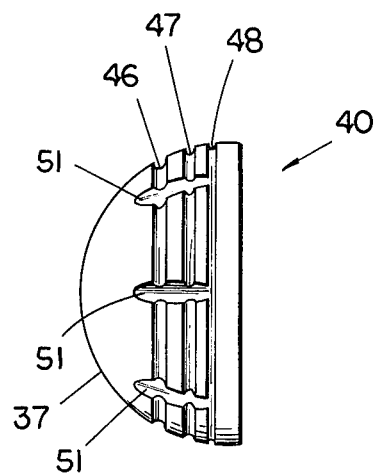
FIG. 9 is an exterior view of the acetabular cup.

One embodiment of the present invention comprises the hip prosthesis 10 shown in FIG. 1. This prosthesis includes a ball head 11 which is connected to a neck 12 along a common axis 13. The neck is connected to a platform 14 which is then connected to an arcuate stem or shaft 15. The prosthesis has a lateral portion 16 and a medial portion 17 and is constructed as one integral unit for insertion into the medullar cavity of a femur, as further shown in FIG. 2 and described below.

As shown in FIG. 4, the platform 14 is oval-shaped and has a lip 18 on its lower lateral portion which extends in the direction of stem 15 and defines a recess 21. When the prosthesis is inserted into the medullar cavity 22 of a femur 23, as shown in FIG. 2, this lip and recess compress the cement 24 into the cavity 22 to securely anchor the prosthesis. The lip further fits precisely against surface 30 of the supporting bone of the femur and acts as a hook in the cement thereby resisting any tendency of the prosthesis to medially tilt during loading. The expanded undersurface 25 of the platform 14 also provides support during loading by resting firmly and precisely against surface 26 of the supporting femur bone.

The platform 14 is oriented at an angle of about 70° relative to the common axis 13 of the neck and ball head as shown in FIG. 1. This places the platform more horizontal and more directly in line with the resultant forces applied on the prosthesis during normal loading and allows these forces to be more evenly distributed across the surface of the platform. This angle also distinguishes the prosthesis of the present invention from any prior art prostheses, as mentioned above, which orient the platform more perpendicular to the axis of the ball head and neck.

The stem 15 is T-shaped in cross section and extends from the lower side of the platform. It also includes three steps, although the exact number is unimportant, which are indicated as 27 through 29 in FIG. 1. As better shown in FIGS. 5 through 7, each step defines a generally horizontal surface 32 through 34 which extends along the anterior and posterior sides of the medial portion of the stem. These squared surface ledges (32 through 34) also compress the cement 24 and provide additional compression-resistant contact surfaces which help to disperse the resultant forces during normal loading. Along with the continuous T-bar of the stem 15 which is also visible in FIGS. 5 through 7 and FIG. 8, the steps further aid in resisting varus or medial tilting, as well as in settling of the prosthesis.

The design of the neck 12, which is oval in cross section as shown in FIG. 3, was also chosen to combat the forces exerted on the prosthesis during loading. This is accomplished by aligning the neck's thicker portion, designated by 35 and 36 in FIG. 3, in the medial and lateral directions, respectively. Such orientation thereby results in significantly strengthening the neck in the medial and lateral directions.

The ball head 11, which is connected to neck 12, is insertable into the acetabular socket of the pelvis once the prosthesis has been securely anchored in the femur. The prosthesis of the present invention is designed to work equally well with a natural acetabular socket or with any variety of artificial acetabular cup. As with all other aspects of the prosthesis, the dimensions of the ball head can be easily varied to adapt to the particular bone structure of the recipient or to the dimensions of the implanted acetabular cup. In the preferred embodiment, the ball head is dimensioned to fit an artificial acetabular cup as further described below.

FIGS. 2, 9, 10 and 11 show the acetabular cup 40 of the preferred embodiment as a dish-shaped receptacle having an outer surface 37, a facial surface 38, and a beveled surface 39. The inner surface 42 is part-spherical, having its center at point 43 and a radius 44 which is equal to the radius 41 of the outer surface 45 of the ball head 11. The cup also has three circumferential grooves 46 through 48 and eight oval grooves 51 which are spaced equally around the circumference of the cup. These grooves provide additional contact surface with the cement 62 and thereby help securely anchor the cup against the prepared surface 63 in the pelvis 61.

Figure 11:
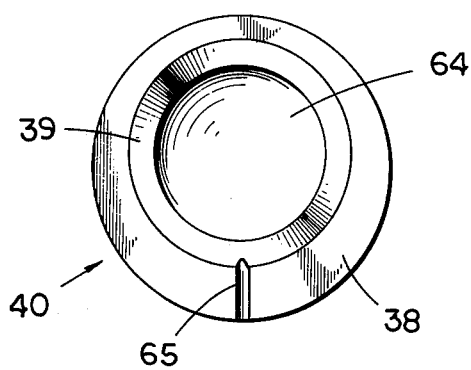
FIG. 11 is a facial view of the acetabular cup in FIG. 9.
Figure 10:
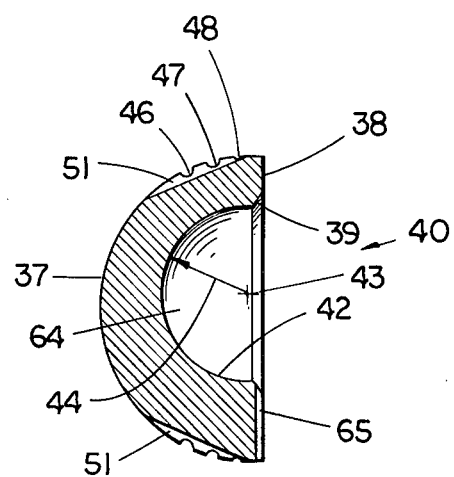
FIG. 10 is a sectional view of the acetabular cup in FIG. 9.

As shown in FIGS. 10 and 11, the inside cavity 64 of the cup is positioned such that facial surfaces 38 varies in width, the greatest width being located adjacent channel 65. By positioning the cup in the pelvis so that channel 65 extends laterally, as shown in FIG. 2, the thickest portion 68 of the cup is positioned directly in line with the resultant forces applied on the cup and ball head during normal loading. This results in greater wearability and longer life for the cup. Furthermore, by designing the eight oval grooves such that they do not extend over the entire outer surface 37 of the cup, the thickness and wearability of the cup are further enhanced.

After the hip prosthesis and cup have been securely cemented into position, the operation is completed by placing the ball head into the inside cavity 64 in the cup.

The material composition of the hip prosthesis of the present invention is highly variable. However, the hip prosthesis of the preferred embodiment was composed of a conventional stainless alloy, such as F-75 orthochrome material, whereas the acetabular cup consisted of polyethylene.

The above description shows the invention to be a platform supported hip prosthesis. While the invention has been fully illustrated and described, the same is understood as not limiting the scope of the invention but only disclosing the preferred embodiment. It is therefore desired that all changes and modifications within the spirit of the invention and the scope of the claims also be protected.

What is claimed is:

1. A platform supported hip prosthesis comprising:
   a. a ball head for insertion into an acetabular socket;
   b. a neck connected to and having a common axis with said ball head;
   c. a platform connected to said neck and oriented at an angle of about 70° relative to the common axis of said neck and said ball head to evenly distribute the forces exerted on the prosthesis during loading, said platform having a medial portion and a lateral portion;
   d. and an arcuate stem, said stem being T-shaped in cross section, connected to and projecting from said platform oppositely of said neck and said ball head and proportioned for reception in the medullar cavity of a femur, said platform having a lip on the lateral portion of said platform, said lip projecting in generally the same direction as said stem and defining a recess which faces toward said stem and is adapted to compress the cement into the medullar cavity during insertion of the prosthesis to securely anchor the prosthesis and thereby resist the tendency for medial tilting during loading.

2. The platform supported hip prosthesis of claim 1 wherein the T-bar of said stem extends along the lateral portion of said stem from said platform to the distal tip of said stem is adapted to resist the tendency for varus tilting during loading.

3. The platform supported hip prosthesis of claim 2 additionally comprising a plurality of steps along the medial portion of said stem both anteriorly and posteriorly, said steps further compressing the cement into the medullar cavity during the securing of said stem and dispersing the resultant loading forces throughout said stem and the cement.

4. The platform supported hip prosthesis of claim 3 wherein said neck is oval in cross section with the thicker portion extending medially and laterally thereby strengthening said neck in those directions.

5. The platform supported hip prosthesis of claim 4 wherein said ball head, said neck, said platform and said stem are an integral unit.

* * * * *